United States Patent [19]

Santilli et al.

[11] Patent Number: 4,726,356
[45] Date of Patent: Feb. 23, 1988

[54] CARDIOVASCULAR AND THORACIC RETRACTOR

[75] Inventors: Albert E. Santilli, Mayfield Heights; Albert N. Santilli, Pepper Pike, both of Ohio

[73] Assignee: Kapp Surgical Instrument, Inc., Warrensville, Ohio

[21] Appl. No.: 797,007

[22] Filed: Nov. 12, 1985

[51] Int. Cl.$^4$ .............................................. A61B 17/02
[52] U.S. Cl. ...................................................... 128/20
[58] Field of Search ................. 128/20, 303 B, 303 R, 128/346

[56] References Cited

U.S. PATENT DOCUMENTS

| | | | |
|---|---|---|---|
| 1,311,313 | 7/1919 | Brix | 128/20 |
| 2,564,118 | 8/1951 | Mahorner | 128/20 |
| 2,670,732 | 3/1954 | Nelson | 128/20 |
| 2,812,759 | 11/1957 | Taylor | 128/20 |
| 3,221,743 | 12/1965 | Thompson et al. | 128/303 B |
| 3,467,079 | 9/1969 | James | 128/303 R |
| 3,810,462 | 5/1974 | Szpur | 128/20 |
| 4,050,464 | 9/1977 | Hall | 128/303 R |
| 4,355,631 | 10/1982 | LeVahn | 128/20 |
| 4,424,724 | 1/1984 | Bookwaltor et al. | 128/20 |

Primary Examiner—Lee S. Cohen
Assistant Examiner—Max F. Hindenburg
Attorney, Agent, or Firm—Pearne, Gordon et al.

[57] ABSTRACT

A cardiovascular retractor is provided which is adapted to be mounted on a thoracic retractor. The cardiovascular retractor includes a clamp support which is mounted along an axis of a thoracic retractor and a retractor blade clamp adjustably secured to a rod of the clamp support. The clamp has a blade grip which grasps a retractor blade. The clamp also includes locking means. When the clamp locking means is not locked, the clamp is adjustable along the clamp support rod, the grip is rotatable in the clamp, the retractor blade is axially adjustable in the clamp, and the retractor blade is rotatable in the clamp. However, when the clamp locking means are locked the clamp locking means securely fix the retractor blade relative to the clamp support so that the retractor blade resists movement and will counteract the tension applied as the cardiovascular retractor is used.

8 Claims, 9 Drawing Figures

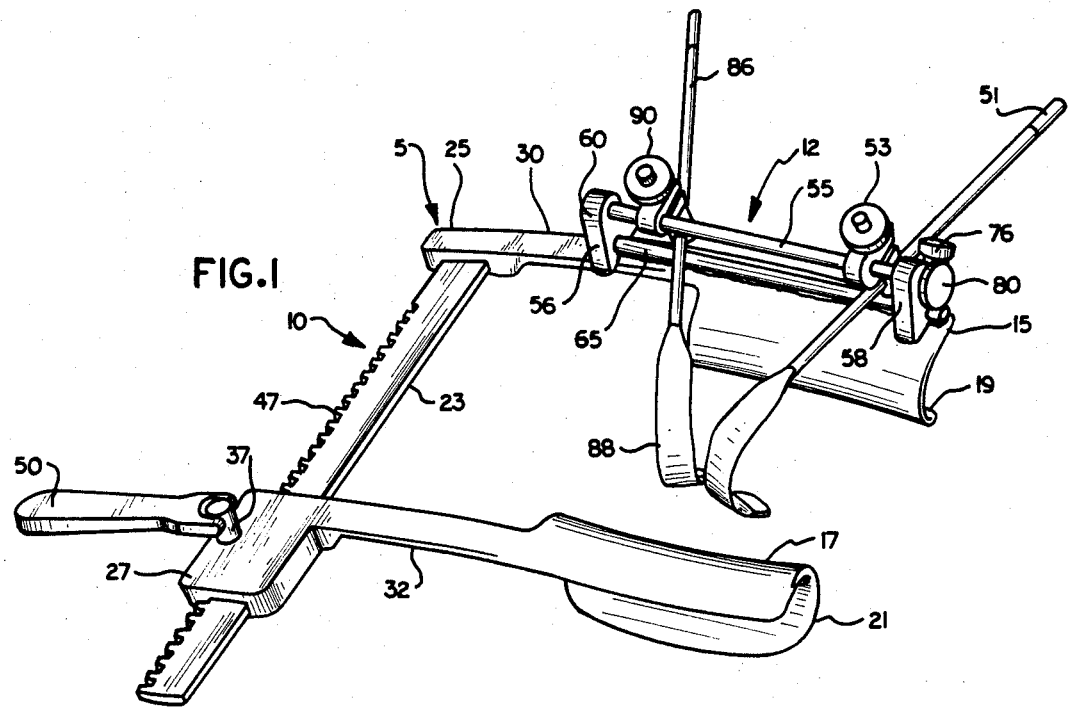
FIG.1
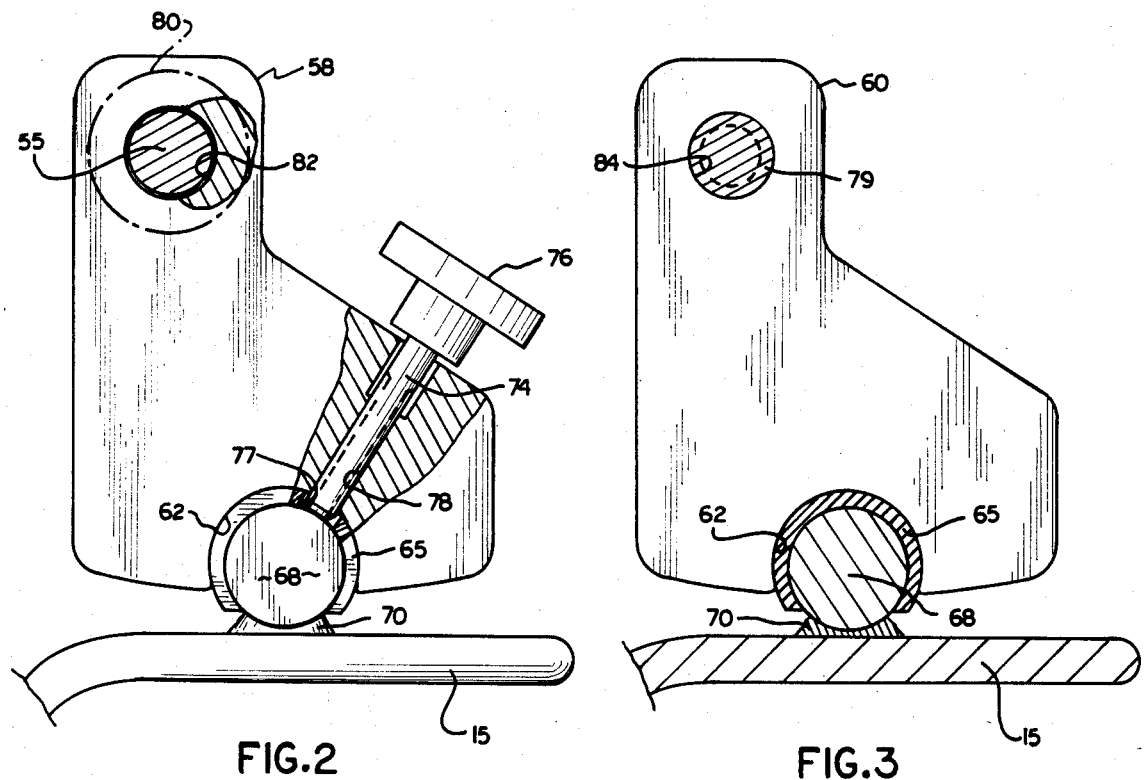
FIG.2
FIG.3

CARDIOVASCULAR AND THORACIC RETRACTOR

BACKGROUND OF THE INVENTION

The invention relates to a cardiovascular and thoracic retractor, and in particular, to a retractor used for open heart surgery. It aids the heart surgeon by letting the surgeon have more control over the surgical procedures; by presenting a retractor having a wide range of adjustability to suit the individual morphology of patients; and by helping to eliminate precious time in the use of the device.

The heart is a hollow muscular pump which lies in the chest cavity in a loose protective sack called the pericardium. The mass of the heart is an extremely powerful thick layer of muscle called the myocardium.

The heart is divided internally to form four chambers. The upper and lower chambers are separated on the right side by the tricuspid valve and on the left side by the mitral valve. Additional valves are located at the outlets from the vessels which leave the heart.

When any of these valves become diseased and fail to operate properly, it may become necessary to perform open heart surgery for correction of the problem. It is possible, for example, to surgically implant artificial heart valves or homograft replacements to replace the natural valves.

During heart surgery, the chest is opened, commonly by an incision several inches long along the axis of the sternum. A sternum retractor is used to maintain exposure of the heart. This retractor includes grips which fit on either side of the chest incision and are used first to open the incision and then to maintain retraction of the ribs and muscles of the chest.

Open heart surgery includes the further step of opening the thick muscular layers of the heart to expose the diseased inner portion of the heart, for example the mitral valve. Commonly a surgical assistant retracts the myocardium or the vessels surrounding the heart using retractor blades. Since the heart is an extremely powerful muscle, the present retraction technique presents the disadvantage that it requires strength and concentration on the part of the surgical assistant to maintain the constant tension necessary to expose the diseased valve. Further disadvantages of this technique are that the heart surgeon relinquishes control to the surgical assistant over this aspect of the operation and that this technique requires an additional person to be involved in the operation.

A device is known from the prior art which mechanically performs the job of the surgical assistant. This device utilizes retractor blades mounted on one grip of the sternal retractor to hold the myocardium open. The retractor blades are mounted at a stationary position relative to the sternal retractor grip. The blades include holes along the handle which lock on hooks on the grip. While several holes are provided along the blade handle and hooks are provided at various distances along the grip to give some flexibility in positioning the blades, the amount of adjustment presented by the known device is limited. In fact, the adjustment is so limited that many surgeons might be deterred from use of the device.

An advantage of the present invention is the wide range of continuous adjustability, not only for the distances which the blades extend from the retractor grip and the placement along the grip, but also for the angle, tilt, and rotation for the retractor blades. This feature is important to allow for the many morphological variations in individuals. Many of these differences cannot be anticipated until the surgeon has opened the chest or heart. The surgeon may even decide to vary the position of the retractors during surgery.

A further advantage of the present invention is that while it allows a great deal of adjustabiity, it is designed to allow the user to go from full adjustability to a locked position very easily.

Another advantage of the present invention is that it is designed for quick and easy assembly and disassembly.

The adjustability and the ease of use of this retractor add to the ultimate goal of any surgeon, and in particular of a heart surgeon; the device helps to simplify a complex operation by eliminating the need for a surgical assistant and allowing the heart surgeon more control and flexibility in performing the operation. Further the device is designed to allow for almost infinite adjustability while decreasing time needed to prepare for open heart surgery and to finish the operation.

SUMMARY OF THE INVENTION

In accordance with the invention, a cardiovascular retractor blade support is supported along an axis of a grip of a thoracic retractor, such as a Cooley sternum retractor. The retractor includes two parallel spaced grips which engage either side of the chest incision and which are mounted at one end perpendicular to a toothed crossbar. A pinion is mounted on one of the grips and engages the teeth of the crossbar for adjustment of the space between the grips.

The retractor blade support includes a rod which extends parallel to the grip between two brackets. The rod supports one or more retractor blade clamps which holds a retractor blade. The clamp permits continuous adjustment of the retractor blade. The retractor blade can be axially extended in relation to the clamp. Further, the blade can be rotated, and the angle of the central axis of the blade with respect to the axis of the rod can be varied.

The clamp is designed to allow flexibility in positioning the retractor blade, but to come to a quick locked position, and also to hold the retractor blade in a locked position with sufficient force to resist the pull of the powerful heart muscle. The retractor blade support is designed to allow for quick and easy assembly and disassembly.

BRIEF DESCRIPTION OF THE DRAWINGS

FIG. 1 shows a perspective view of the cardiovascular and thoracic retractor in accordance with the invention;

FIG. 2 shows an end view of the first retractor blade support bracket with portions broken away;

FIG. 3 shows an end view of the second retractor blade support bracket;

DETAILED DESCRIPTION OF THE DRAWINGS

Figure 4:
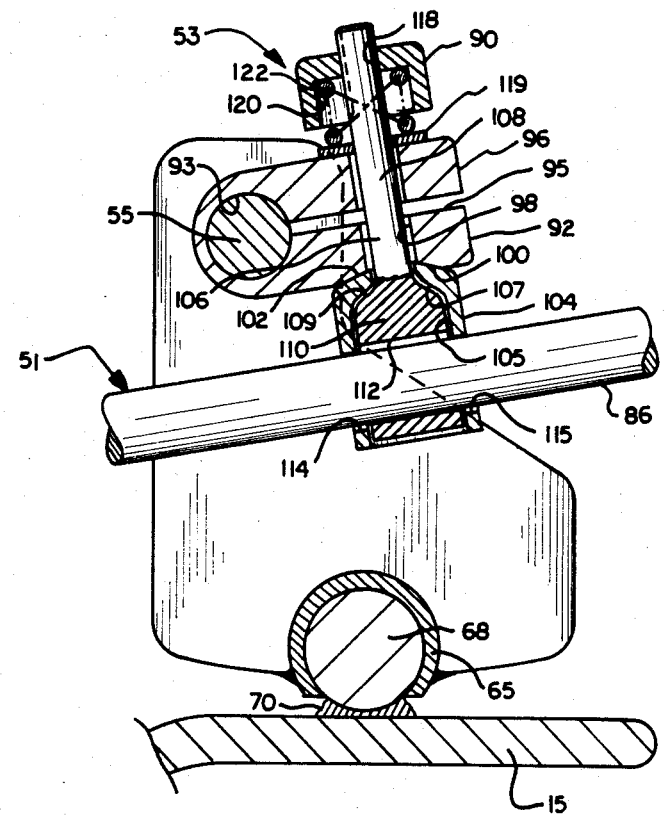
FIG. 4 shows a vertical cross-section of the retractor blade clamp.

The invention concerns a cardiovascular and thoracic retractor 5 comprising a thoracic retractor 10 and a cardiovascular retractor 12 mounted on the thoracic retractor 10. The cardiovascular retractor 12 of the present invention is illustrated with a Cooley sternum retractor; however it should be understood that other sternum retractors could be used. The thoracic retractor 10 includes a first grip 15 and a second grip 17 having a first cuff 19 and a second cuff 21, respectively. The cuffs 19, 21 engage either side of the chest incision to expose the internal organs during the operation. The grips 15, 17 are mounted in a spaced parallel position to each other by means of a toothed crossbar 23 which extends perpendicularly between a distal portion 25, 27 of the first and second grips 15, 17. A flat arm portion 30, 32 extends between the distal portion and the cuff of each grip. The first grip 15 is fixed relative to the crossbar 23.

The second grip 17 includes on its distal end 27 a pinion. The pinion has a pivot 37 which extends through a slot (not shown) in the distal portion 27 of the grip 17. The pivot 37 is attached to a disc (not shown), the disc having two extending pins (not shown) spaced at a proper distance for engagement of the teeth 47 on the toothed crossbar 23. The pivot 37 has at the opposing end a handle 50 which is pivotally mounted on a pin (not shown) extending through the pivot 37 so that the pivot 37 can be rotated by the handle 50.

As the handle 50 is rotated, the extending pins engage the teeth 47 of the crossbar 23 forming a rack and pinion system, whereby the distance between the grips 15, 17 can be increased. When the pivot 37 is in the proper position the retractor is locked to resist the forces which would tend to close the incision.

The cardiovascular retractor 12 includes a clamp support 56 adapted to be mounted on the thoracic retractor 10 along the axis of the first grip 15. The cardiovascular retractor 12 further comprises one or more retractor blade clamps 53 secured to the clamp support 56. The retractor blade clamp 53 engages a retractor blade 51.

The retractor blade support 56 includes a first and second bracket 58, 60. Both brackets include a groove 62 at the lower end. A sleeve 65 is housed in the groove 62 and extends between the brackets 58, 60 to hold the brackets in a spaced parallel position. The sleeve 65 provides rigidity for the rod 55 which extends between the upper ends of the brackets 58, 60.

The sleeve 65 forms a female member which mates with a male member protruding from the thoracic retractor 10. In this case the male member is a bar 68 which is joined to the upper side of the first grip 15, as for example by weld 70. Of course, the clamp support 56 could include the male member and the thoracic support 10 could include the female member.

A threaded pin 74 having a knob 76 engages a threaded opening 78 in the first support 58. The pin 74 extends through a hole 77 in the sleeve 65 to bear against the bar 68 when the pin 74 is rotated to its locked position. This allows the retractor blade support 56 to be secured to the bar 68 on the thoracic retractor 10.

The rod 55 has at one end threads 79 and a grip 80 at the other end. The rod 55 is fed through a hole 82 in the first bracket 58 (and through a bore 93 in the clamp 53) until the threads 78 of the rod 55 engage a threaded opening 84 in the second bracket 60 as can be seen in FIG. 3. The rod 55 is screwed in position by turning the grip 80.

The retractor blade 51 consists of an elongate handle 86 and a flat curve 88 for retention of the vessels or organ. The handle 86 is held in position relative to the retractor blade support 56 by means of the clamp 53 which grasps the handle 86 about the central axis of the retractor blade 51. One retractor blade may be mounted on the retractor blade support; however, more commonly, two or more retractor blades will be secured to the retractor blade support, each blade 51 being held by its own clamp 53. The clamp 53 is mounted on the rod 55 and is positionable along the axis of the rod 55.

The clamp 53 is constructed to allow a great deal of adjustability in the position of the retractor blade 51. When the clamp 53 is not locked, the clamp 53 can be slid along the axis of the rod 55. Further, the clamp 53 may be rotated about the axis of the bar 55 to vary the angle of the blade 51 and more specifically of the angle between the plane extending through the axis of the blade 51 and tangential to the flat curve 88 and the plane extending through the axis of the rod 55. The blade 50 is held in a blade grip 106 which is rotatable about its axis in the clamp 53 to vary the angle formed between the axis of the blade 50 and the axis of the rod 55. It is possible as well to slide the handle portion 86 of the blade in or out of the clamp 53 so that the curve portion 88 may be axially extended or retracted. Further, the retractor blade 51 may be rotated about its central axis to vary the tilt of the curve portion 88 of the retractor blade 51.

The clamp 53 is designed to allow a great deal of adjustability as has been explained, but to come into a locked position, eliminating all adjustment by a relatively slight change in the clamp. The position of the retractor blade 51 becomes fixed when the knob 90 is rotated to cause the clamp to lock.

A detailed drawing of the clamp 53 is shown in FIG. 4. The clamp 53 includes a collar 92 having a bore 93 which engages the rod 55. A slot 95 extends through a flange portion 96 of the collar 92 to the bore 93. A second bore 98 extends through the flange portion 96 of the collar 92, axially transverse to the slot 95 and spaced apart from the first bore 93. The second bore 98 ends in a conical indentation 100 which mates with the conical portion 102 of a sleeve 104. The sleeve 104 has a concentric hollow portion 105.

A blade grip 106 having a pin portion 108 and a vice portion 110 extends through the second bore 98 and the sleeve 104. The grip 106 has a central axis which is aligned with the axis of the bore 98 and the sleeve 104. The grip 106 and the vice portion 110 includes an opening 112 which extends through the grip 106. The axis of the opening 112 is transverse to the axis of the rod 55. The sleeve 104 also includes openings 114 and 115 substantially aligned with the opening 112 so that the handle 86 of the retractor blade 51 extends through the openings 112 and 114, and 115 respectively of the blade grip 106 and sleeve 104. The knob 90 includes a threaded hole 118 which engages the threads on the pin portion 108 of the grip 106. The knob 90 further is hollow to form a recess 120 which houses a spring 122. The spring 122 biases the knob outward by cooperating with a spacer 119 which rests against the top of the collar 92.

The rotation of the knob 90 which engages the threads in the pin portion 108 of the grip 106 causes the blade grip 106 to be raised in the collar 92. This forces the sleeve 104 against the collar 92 as the shoulder 109 of the grip 106 engages a corresponding shoulder 107 of the sleeve 104. The retractor blade 51 is locked from rotational movement about the axis of the grip 106 as the conical portion 102 of the sleeve 104 engages the conical indentation 100 of the collar 92. This has the further effect of locking the collar 92 from rotational or axial movement relative to the rod 55 by closing the slot 95 and causing the first bore 93 to tighten around the surface of the rod 55.

The position of the retractor blade 51 is locked radially along its own axis, and further from rotation about its central axis by the vice portion 110 and the sleeve 104. As the blade grip 106 is raised in relation to the sleeve 104, the handle 86 of the retractor blade 51 is locked on the bottom side by the bore 112 of the vice 110, and on the top side by the openings 114, 115 of the sleeve 104. This locks the retractor blade 51 against axial movement and rotation.

The spring 122 biases the grip 106 upward relative to the collar 92 and eliminates play in the mechanism of the clamp 53. The clamp 53 is designed so that the turning of the knob 90 causes all the possible adjustments to be locked.

Figure 5:
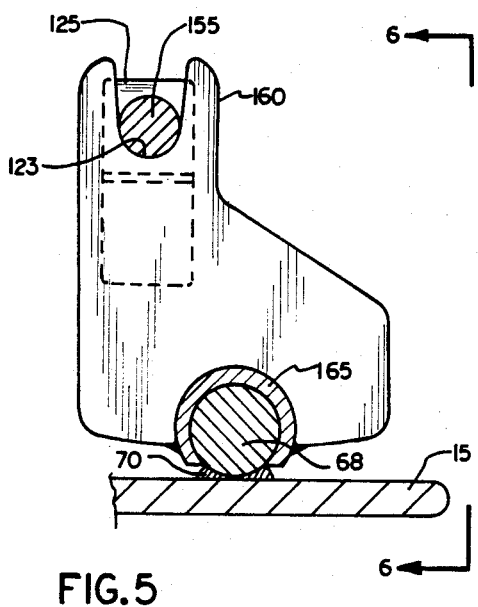
FIG. 5 shows an end view of a retractor blade support bracket of the second embodiment of the invention.
Figure 6:
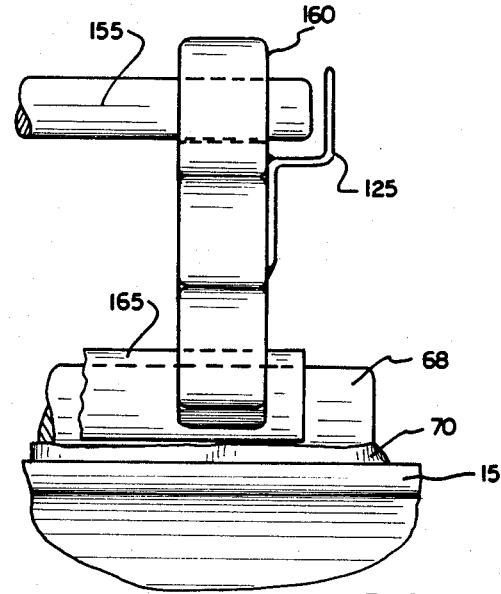
FIG. 6 shows a front view of the retractor blade support bracket of the second embodiment taken along line 6—6.

FIGS. 5 and 6 show a second embodiment of the invention, wherein the first and second supports 160 include a recess 123 having a shape designed for snug engagement of the rod 155 but also designed so that the rod 155 may be easily disengaged from the retractor blade support by simply pulling the rod 155 up out of the recess 123. Likewise, the rod 155 can simply be dropped into the recess 123. The supports 160 also include guards 125 for the lateral positioning of the rod 155 in the recess 123.

Use of the device is envisioned as follows: prior to surgery the cardiovascular retractor 12 is assembled. The rod 55 is threaded through the hole 82 in the first support 58, through the bore 93 in the clamp 53, and engages the threaded opening 84 in the second support 60. The grip 80 of the rod 55 is turned to lock the rod 55 into position.

During surgery, the thoracic cavity will be opened as usual using the thoracic retractor 10. The cardiovascular retractor 12 is subsequently mounted on the thoracic retractor 10 by positioning the sleeve 65 of the retractor blade mount 56 on the bar 68 on the grip 15 of the thoracic retractor 10. The retractor blade mount 56 is locked on the bar 68 by turning the knob 76.

The user slides the clamp 53 into the proper position along the axis of the rod 55 and positions the retractor blade 51 as desired, moving the blade into the proper position for surgery. The knob 90 is tightened and the blade 51 is subsequently held in the desired position. This embodiment is designed so that the rod 55 cannot inadvertently be dislocated from the brackets 58, 60.

When surgery has been completed, the knobs 90 and 76 are loosened, the retractor blade 51 is disengaged, and the retractor blade support 56 can be lifted from the bar 68.

The embodiment shown in FIGS. 5 and 6 is used in a similar manner, except that the rod 155 is not threaded through openings in the first and second brackets prior to surgery, but rather engaged in the recess 123 in the first and second brackets 160 after the blade support 156 is mounted on the grip 15. This embodiment is designed so that the rod 155 is easily disengaged from the brackets.

Figure 7:
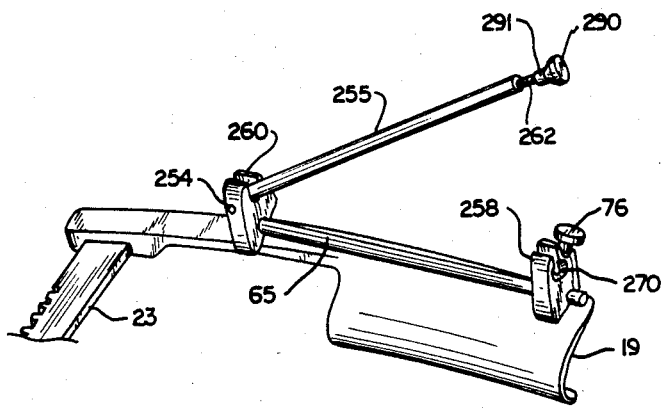
FIG. 7 shows a perspective view of a portion of the retractor in accordance with a third embodiment of the invention.
Figure 8:
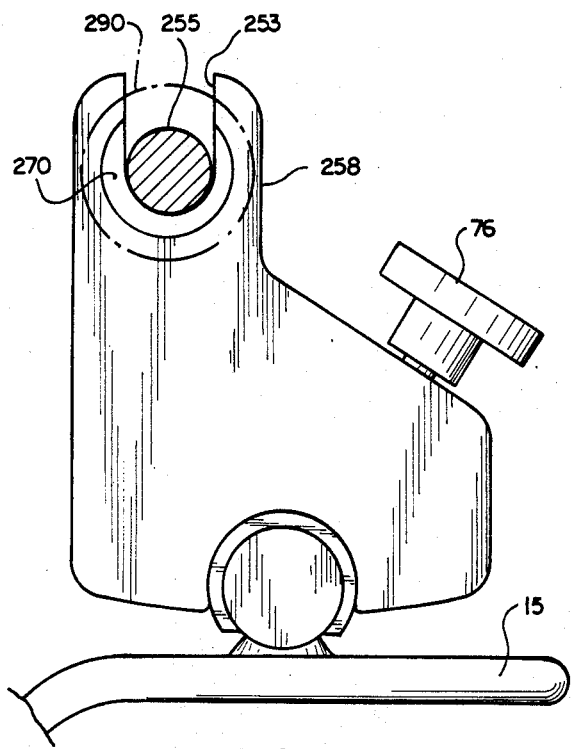
FIG. 8 shows an end view of the first retractor blade support bracket of the third embodiment of the invention.
Figure 9:
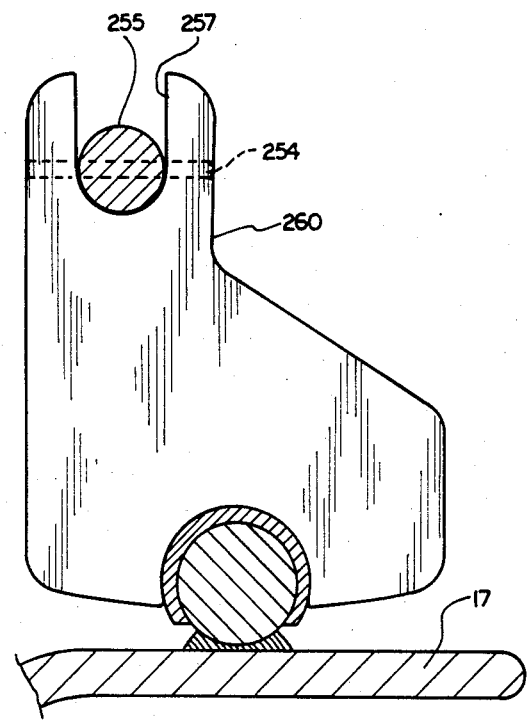
FIG. 9 shows an end view of the second retractor blade support bracket for the third embodiment with portions broken away.

Another embodiment of the invention is shown in FIGS. 7, 8 and 9. This embodiment is also used in a manner similar to that described, except that the rod 255 engages a slot 253 in the first bracket 258 and is pivotably joined at the other end in a slot 257 in the bracket 260 as by the in 254. The end of the rod 255 which engages the slot 253 in the first bracket 260 includes a threaded portion 262 which cooperates with a knob 290. The knob 290 is threaded onto the rod 255 after the clamps 53 have been slide onto the rod 255. The knob 290 includes a sleeve portion 291 which engages a counterbore 270 portion of the slot 253. As the knob 290 is tightened on the rod 255 the sleeve portion 291 grips the counterbore 270 and locks the rod 255 into position between the brackets 258, 260.

Although the preferred embodiment of this invention has been shown and described, it should be understood that various and modifications and rearrangements of the parts may be resorted to without departing from the scope of the invention as disclosed and claimed herein.

What is claimed is:

1. A cardiovascular retractor comprising a thoracic sternum retractor including a pair of arms and a crossbar interconnecting said arms, a second retractor comprising a rod having opposite ends, a pair of brackets each secured to the opposite ends of said rod, connecting means extending between and attached to said brackets parallel to and spaced from said rod, means mounting said second retractor on one of said arms with said rod generally parallel to the arm, a blade clamp mounted on said rod between said brackets and constructed and arranged to be movable along said rod, a retractor blade having a handle and mounted on said blade clamp to permit movement of said handle along its axis with respect to said clamp, and gripping means constructed and arranged to fixedly position said blade handle with respect to said clamp and said clamp with respect to said rod.

2. A cardiovascular retractor as set forth in claim 1, wherein said second retractor is removably mounted on said one arm.

3. A cardiovascular retractor as set forth in claim 2, wherein said connecting means is a sleeve and said removable mounting means comprises said sleeve and a bar secured to said one arm and received in said sleeve to permit movement of said second retractor along the axis of said bar.

4. A cardiovascular retractor as set forth in claim 3, including means to clamp said sleeve to said bar to prevent axial movement.

5. A cardiovascular retractor as set forth in claim 1, wherein said rod is removably attached to at least one of said brackets.

6. A cardiovascular retractor as set forth in claim 5, wherein said releasable attachment comprises aligned bores in both of said brackets to receive said rod, one of said bores having internal threads and the adjacent rod end having external threads in engagement with said internal threads.

7. A cardiovascular retractor as set forth in claim 5, wherein said releasable attachment comprises a recess on each of said brackets arranged to snugly receive said bar, and guard means to prevent movement of said rod along its axis with respect to said brackets.

8. A cardiovascular retractor as set forth in claim 5, wherein said rod is pivotally connected at one end to one bracket for rotation about an axis perpendicular to the axis of the rod, and clamp means on the other end of said rod engageable with the other bracket.

* * * * *

UNITED STATES PATENT AND TRADEMARK OFFICE
CERTIFICATE OF CORRECTION

PATENT NO. : 4,726,356

DATED : February 23, 1988

INVENTOR(S) : Santilli et al.

It is certified that error appears in the above-identified patent and that said Letters Patent is hereby corrected as shown below:

On the face of the patent, item [75] should read as follows:

[75] Inventors: Albert E. Santilli, Mayfield Heights;
Delos M. Cosgrove III, Hunting Valley,
both of Ohio Signed and Sealed this Eighteenth Day of October, 1988

Attest:

DONALD J. QUIGG

*Attesting Officer*  *Commissioner of Patents and Trademarks*